United States Patent [19]

Walker

[11] 4,256,759
[45] Mar. 17, 1981

[54] ALPHACARBAMOYL-PYRROLPROPIONI-TRILES

[75] Inventor: Gordon N. Walker, Morristown, N.J.

[73] Assignee: Ciba-Geigy Corporation, Ardsley, N.Y.

[21] Appl. No.: 142,489

[22] Filed: Apr. 21, 1980

Related U.S. Application Data

[63] Continuation-in-part of Ser. No. 46,063, Jun. 11, 1979, abandoned.

[51] Int. Cl.³ .................. C07D 207/337; A61K 31/40
[52] U.S. Cl. .............................. 424/274; 260/326.47; 260/326.5 J; 548/248
[58] Field of Search ..................... 260/326.47; 424/274

[56] References Cited
U.S. PATENT DOCUMENTS 4,061,767  12/1977   Ertel et al. ........................... 424/282

Primary Examiner—Mary C. Lee
Attorney, Agent, or Firm—Theodore O. Groeger

[57] ABSTRACT

1-Substituted-$\beta$-oxo-$\alpha$-phenylcarbamoyl-pyrrolpropionitriles, e.g. those of the formula

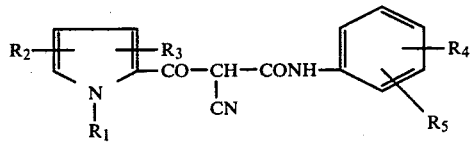

$R_1$ = alkyl or aralkyl
$R_{2,3}$ = H or alkyl
$R_{4,5}$ = H, alkyl, alkoxy, OH, halo or $CF_3$ their alkylenol ethers or alkanoylenol esters and salts thereof are antiinflammatory and antiarthritic agents.

9 Claims, No Drawings

ALPHACARBAMOYL-PYRROLPROPIONITRILES

CROSS-REFERENCE TO RELATED APPLICATION

This is a continuation-in-part of application Ser. No. 046,063, filed June 11, 1979, now abandoned.

BACKGROUND OF THE INVENTION

Specially substituted "cyanoacetic acid anilides" and related "isoxazolyl carboxylic acid anilides", e.g. those of the formulae

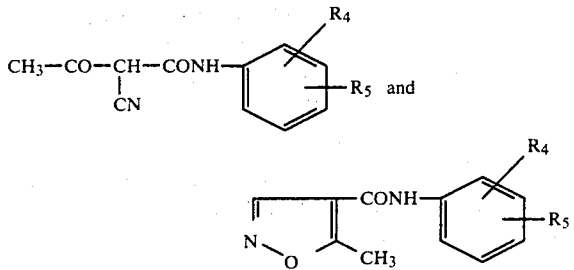

"are non-ulcerogenic antiphlogistics and analgesics" according to Belgian Pat. Nos. 842,688; 842,689; 849,343; 861,500 or U.S. Pat. No. 4,061,767 respectively.

Surprisingly, said new pyrrolpropionitriles offer distinct therapeutic advantages, e.g. with regard to activity spectrum and tolerability, over said known anilides; as well as the very old benzoyl analogs thereof, e.g. as described in J. Am. Chem. Soc. 35, 959 (1913).

SUMMARY OF THE INVENTION

The present invention concerns and has for its object the provision of new substituted $\beta$-oxo-$\alpha$-phenylcarbamoyl-pyrrolpropionitriles, preferably of those corresponding to Formula I

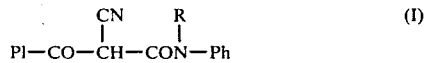

wherein Pl is 2- or 3-pyrrolyl substituted in 1-position by lower alkyl or Ph-lower alkyl and being unsubstituted in the remaining 3 positions, or substituted therein by lower alkyl and/or one carboxy or lower carbalkoxy; R is hydrogen or lower alkyl, and Ph is phenyl, unsubstituted or substituted by one to three identical or different members selected from lower alkyl, lower alkoxy, lower alkylthio, hydroxy, halogeno, trifluoromethyl, nitro, amino or lower alkanoylamino; a lower alkylenol ether or alkanoylenol ester, or a salt thereof derived from a pharmaceutically acceptable base; as well as of corresponding pharmaceutical compositions and of methods for the preparation and application of these products, which are useful antiinflammatory and antiarthritic agents.

DESCRIPTION OF THE PREFERRED EMBODIMENTS

Both of said pyrrolyl and phenyl groups Pl and Ph are preferably C-unsubstituted, but may also be substituted, more particularly by but one or two, of the same or different members selected from the group consisting of lower alkyl, e.g. methyl, ethyl, n- or i-propyl or -butyl. Ph, moreover, may also be substituted by lower alkoxy, e.g. methoxy, ethoxy, n- or i-propoxy or -butoxy; lower alkylthio, e.g. methylthio or ethylthio; hydroxy; halogeno, e.g. fluoro, chloro or bromo; trifluoromethyl; nitro; amino or lower alkanoylamino, e.g. acetylamino or propionylamino. Pl, moreover, may also contain one carboxy or lower carbalkoxy group, e.g. carbomethoxy or carbethoxy, preferably in the 3- or 4-position.

The lower alkyl or Ph-alkyl groups in the 1-pyrrole position are above all methyl, but also ethyl, n- or i-propyl or -butyl; benzyl, 1- or 2-phenethyl, 1-, 2- or 3-phenylpropyl, unsubstituted or substituted as shown for Ph above.

The other N-substituent R is preferably hydrogen, but also one of said alkyl groups listed above.

As used herebefore and hereinafter, the term "lower" defines such groups, or compounds respectively, containing up to 7, preferably up to 4, and especially but 1 or 2 carbon atoms.

The $\beta$-hydroxy-tautomers of Formula I are sufficiently acidic to form said lower alkylenol ethers, alkanoylenol esters, or salts with pharmaceutically acceptable bases, such as alkali metal, alkaline earth metal, copper or zinc hydroxides; ammonia, mono-, di- or tri-lower (alkyl or hydroxyalkyl)-amines, alkyleneimines or alkylenediamines, e.g. sodium, potassium, magnesium, ammonium, mono-, di- or tri-(methyl, ethyl or hydroxyethyl)-ammonium, pyrrolidinium, ethylenediammonium or morpholinium salts; or various hydrates thereof.

The compounds of the invention exhibit valuable pharmacological properties, primarily antiinflammatory and antiarthritic activity. This can be demonstrated by in-vitro or in-vivo tests, using for the latter advantageously mammals, such as rats, guinea pigs or dogs, as test objects. The compounds of the invention can be administered to the animals either enterally, preferably orally; parenterally, e.g. subcutaneously or intravenously; or topically, for example, in the form of aqueous or oily solutions or starchy suspensions. The applied dosage may range between about 0.1 and 100 mg/kg/day, preferably between about 1 and 50 mg/kg/day, advantageously between about 2 and 25 mg/kg/day. The tests chosen are among the classical assay methods for said activity, such as the carrageenin paw-edema, or adjuvant arthritis test in rats, the canine synovitis or ultraviolet erythema assays, or more recent tests, such as neutral protease inhibition, described in Arthritis Rheum. 17, 47 (1974), or inhibition or leukocyte chemotaxis, described in Ann. N.Y. Acad. Sci., 256, 177 (1975); or decrease of neutrophil adherence, described in Amer. J. Med. 61, 597 (1976); or inhibition of prostaglandin synthetase, described in Biochem. 10, 2372 (1971).

Illustrative is the following test method, yielding relevant data: Male Charles River rats, weighing 250-300 g are immunized by intradermal injections of 0.1 ml Bacillus Calmette Guerin (BCG) vaccine. One week later, the animals are injected with 10 ml of a sterile 2% rice starch solution intraperitoneally, to induce the accumulation of macrophages. On day 11 after immunization, the animals are sacrificed and peritoneal macrophages collected with 20 ml of Gey's balanced salt solution containing heparin (25 units/ml). The harvested cells are centrifuged at 1000 RPM for 10 minutes, washed with 50 ml more of Gey's solution at the same speed and time, and then they are resuspended in Gey's solution containing 0.1% human serum albumin (Fraction V, Sigma Co. pH=7.1) to yield a concentration of $2 \times 10^6$ cells/ml.

The test substances are dissolved in dimethylacetamide to yield a $1 \times 10^{-2}$ M solution. Subsequent dilutions are made with Gey's solution, and they are finally added to the above cell suspension to yield the appropriate final concentrations of $10^{-4}$, $10^{-5}$, $10^{-6}$ and $10^{-7}$ M. Said substances remain with the cells after the suspensions are distributed over the upper compartment of the modified Boyden chemotaxis chambers.

E. coli lipopolysaccharide (Difco) activated rat serum (1/10 dilution at pH=7.1) is used as the chemotactic agent and placed in the lower compartment of said chambers. The cell compartment of the chamber is separated from the chemotactic solution by a 8 micron pore size cellulose filter membrane, the chambers are set up in triplicate and incubated for 5 hours at 37° C. Cell suspensions alone, without test compound, serve as controls for cell-migration. After incubation, the filters are removed, fixed and stained with Weigert's iron hematoxylin, and four fields of the lowermost surface of the filter are examined microscopically at a magnification of 320. The average of the number of neutrophils counted in those four fields is used as an index of chemotactic activity, and indomethacin or levamisole are also run in said procedure as reference compounds.

Thus, for example, the 1-methyl-β-oxo-α-phenylcarbamoyl-2-pyrrolpropionitrile, a representative member of the compounds of this invention, or said enol ethers, esters, salts and congeners thereof corresponding to Formulae I or II, are highly active in rats at p.o. doses as low as 2 mg/kg/day in the adjuvant arthritis assay. Its influence in modulating the in vitro chemotactic activity of BCG-immunized macrophages is significant at concentrations down to $10^{-5}$ M and $10^{-6}$ M, resulting in an enhanced chemotactic response of the macrophages. In contrast, indomethacin does not influence macrophage chemotaxis, while levamisole, a known immunopotentiator, produces increased migration at final concentrations of $10^{-3}$ M to $10^{-5}$ M.

Accordingly, the compounds of this invention show good activity in said tests, which distinguish them from other nonsteroidal antiinflammatory drugs. However, the activity exhibited in the macrophage chemotaxis test is similar to that of levamisol, which has been classified as a disease modifying antirheumatic drug. Therefore, the compounds of this invention, exhibiting both indomethacin- and levamisole-type activities, are useful antiinflammatory and antiarthritic agents, for example, in the treatment or management of inflamed arthritic and/or dematopathologic conditions.

Particularly useful are compounds of Formula I, wherein Pl is 1-lower (alkyl or Ph-alkyl)-2 or 3-pyrrolyl, unsubstituted in the remaining positions or substituted therein by one or two lower alkyl groups, or one carboxy or lower carbalkoxy group; Ph is phenyl or phenyl substituted by one or two of the same or different members selected from lower alkyl, lower alkoxy, lower alkylthio, hydroxy, halogeno, trifluoromethyl, nitro amino and lower alkanoylamino; and R is hydrogen or lower alkyl; or a lower alkylenol ether or alkanoylenol ester, or a salt thereof derived from a pharmaceutically acceptable base.

Preferred compounds of the invention are those of Formula II

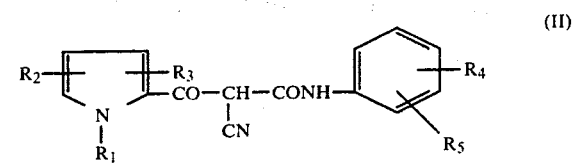

wherein $R_1$ is lower alkyl; each of $R_2$ and $R_3$ is hydrogen or lower alkyl; and each of $R_4$ and $R_5$ is hydrogen, lower alkyl, lower alkoxy, hydroxy, halogeno or trifluoromethyl; or a salt thereof derived from a pharmaceutically acceptable base.

Outstanding are compounds of Formula II, wherein $R_1$ is alkyl with up to 4 carbon atoms; each of $R_2$ and $R_3$ is hydrogen; and each of $R_4$ and $R_5$ is hydrogen, alkyl or alkoxy with up to 4 carbon atoms each, fluoro, chloro or trifluoromethyl; or a salt thereof derived from a pharmaceutically acceptable base.

Most preferred are those compounds of Formula II, wherein $R_1$ is methyl; each of $R_2$ and $R_3$ is hydrogen; and each of $R_4$ and $R_5$ is hydrogen, methyl, methoxy, fluoro, chloro or trifluoromethyl; or the sodium, potassium, calcium, triethylammonium or trishydroxyethylammonium salt thereof; one of $R_4$ and $R_5$, different from hydrogen, being preferably in the para-position.

The compounds of the invention are prepared according to conventional methods, for example, by:

(a) adding the compounds of the formulae

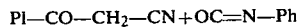

and, if desired, N-substituting a resulting compound with a reactive ester of R—OH, or (b) condensing compounds of the formulae

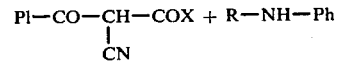

wherein X is lower alkoxy, lower alkanoyloxy or halogeno, or (c) condensing compounds of the formulae

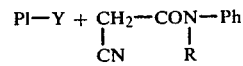

wherein Y is lower alkoxycarbonyl, halocarbonyl or cyano and hydrolysing resulting imines, or (d) isomerizing compounds of the formula

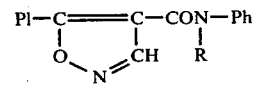

with a strong base and, if desired, converting any resulting product of Formula I into another compound of the invention.

The addition of the isocyanate according to item (a) is preferably carried out according to said Belgian patents or according to U.S. Pat. No. 3,905,997, i.e., in the absence or presence of an inorganic or organic base, such as sodium hydride, or in the presence or absence of a polar solvent, such as an ether, e.g. diethyl ether or tetrahydrofuran, and/or an amide or sulfoxide, e.g.

dimethylformamide or -sulfoxide; advantageously at raised temperatures, e.g. at about 150° if no base is used.

The preferred process according to the invention is generally performed thus: The suspension of said nitrile in an aromatic hydrocarbon, e.g. warm toluene, is treated with a slight molar excess of an anhydrous tri-lower alkylamine, preferably triethylamine, and then a molar equivalent of the phenylisocyanate Ph—N=CO is added, or a solution thereof in the polar solvents mentioned above, e.g. dimethylsulfoxide. After stirring for about 2-12 hours at room temperature, the reaction mixture is reduced in volume by evaporation without excessive warming e.g. up to 100°. The residue is taken up in an alkanol, e.g. methanol, and the solution treated with an excess of diluted aqueous acid, e.g. 0.3 N hydrochloric acid, and the crude, crystalline products are collected, washed with water, dried, triturated and/or recrystallized from appropriate solvents, such as lower alkanols, alkanones, dialkyl ethers and/or alkyl alkanoates, e.g. methanol, acetone, diethyl ether and/or ethyl acetate.

The amination according to item (b) is also carried out in the usual manner, advantageously between room temperature and about 150°, either with equivalent amounts of the reactants, preferably when the ester is used, or with an excess of the amine, or in the presence of another base, such as a tertiary amine, e.g. a tri-lower alkylamine or pyridine, when the halide or anhydride is used, in order to neutralize the generated acid. The lower alkanol, generated in the reaction with said esters, is preferably distilled off together with diluent, such as an aromatic hydrocarbon, e.g. benzene, toluene or xylene.

The condensation according to item (c) is advantageously performed with the utilization of alkali metals, their lower alkoxides or preferably hydrides, e.g. sodium hydride, in said polar solvents, preferably dimethylformamide or -sulfoxide. This condensation is analogous to the preparation of said nitrile starting materials according to items (a) and (b), which is illustrated by the respective examples herein.

Finally, the isomerization according to item (d) is taking place in the presence of said strong inorganic or organic bases, e.g. alkali metal hydroxides or tri-lower alkyl-aralkylammonium hydroxides, e.g. trimethyl-benzylammonium hydroxide.

The compounds of Formula I, so obtained, can be converted into each other according to methods known per se. Thus, for example, resulting enols can be etherified, e.g. with lower diazoalkanes, or esterified, e.g., with lower alkanoic acid anhydrides; or salified with said pharmaceutically useful bases, e.g. aqueous alkali metal hydroxides, advantageously in the presence of an ethereal or alcoholic solvent respectively, such as a lower alkanol. From the solutions of the latter the salts may be precipitated with said ethers, e.g. diethyl ether or tetrahydrofuran, at moderate temperatures, e.g. below 100°. Resulting salts may be converted into the free compounds by treatment with acids as mentioned above. Also a nitro group within Ph can be reduced, for example, with catalytically activated hydrogen, e.g. in the presence of nickel or palladium catalysts, to yield the corresponding amino compounds, which may be acylated either as shown above, or with lower alkanoic acid halides or alkyl esters. The starting materials used are known, or if new, can be prepared according to the methods used for the known analogs mentioned in the "Background" paragraph, or illustrated by the examples herein.

The above reactions are otherwise carried out according to standard methods, in the presence or absence of diluents, preferably such as are inert to the reagents and are solvents thereof, of catalysts, condensing or neutralization agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives, preferably alkali metal or trialkylammonium salts of said enols. Said isocyanates may also be formed from the corresponding acid azides; and mixed anhydrides from the corresponding acids and simple alkanoic acid anhydrides. In said processes of the invention those starting materials are advantageously selected, which yield the above-described preferred embodiments of the invention, especially those corresponding to Formula II.

The pharmacologically active compounds of the invention are useful in the manufacture of pharmaceutical compositions containing an effective amount thereof in conjunction or admixture with excipients suitable for either enteral, parental or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tables also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories or topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade and, all parts wherever given are parts by weight. If not otherwise stated, evaporations are carried out under atmospheric pressure.

EXAMPLE 1

To the suspension of 12.9 of 1-methyl-$\beta$-oxo-2-pyrrolpropionitrile in 150 ml of dry toluene and 10.1 g of anhydrous triethylamine, 10.7 g of phenylisocyanate are added while stirring. After all solids are dissolved, the dark red solution is allowed to stand 30 minutes at room temperature, 5 minutes on the steam cone and at room temperature overnight. The mixture is evaporated on the steam cone, the residue taken up in methanol and the solution poured into the mixture of 25 ml of 5 N hydrochloric acid and 600 ml of water. The light brown crystals formed are collected, washed with water, triturated with ethanol and recrystallized from about 2200 ml of methanol, to yield the 1-methyl-β-oxo-α-phenylcarbamoyl-2-pyrrol-propionitrile of the formula

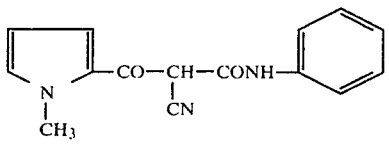

melting at 174°–175°.

The starting material is prepared as follows: The solution of 28 g of 1-methylpyrrole-2-carboxylic acid in 20 ml of dimethylformamide is added to the suspension prepared from 12 g of 50% sodium hydride in mineral oil, washed with petroleum ether and suspended in 50 ml of dimethylformamide, while stirring and cooling. Thereupon 30 ml of methyl iodide are added and stirring is continued at ambient temperature. Another 10 ml of methyl iodide are added after the initial exothermic reaction has subsided. After standing overnight, the mixture is treated with water, extracted with diethyl ether, the extract washed with aqueous sodium carbonate and water, dried and evaporated, to yield the 1-methylpyrrole-2-carboxylic acid methyl ester as an oil.

The solution of 28 g thereof in 50 ml of acetonitrile is added to the suspension prepared from 19 g of 50% sodium hydride in mineral oil, washed with petroleum ether and suspended in 50 ml of dimethylformamide, while stirring. After the exothermic reaction subsided, the mixture is warmed on the steam cone for 15 minutes, during which a further, vigorously effervescent reaction occurs. The thick, red-brown suspension is diluted with another 50 ml of dimethylformamide and allowed to stand overnight at room temperature. It is reheated for 5 minutes on the steam cone, again cooled, and combined with water. The aqueous solution is filtered, washed once with diethyl ether and acidified with hydrochloric acid. The crystals are collected, washed with water, dried, triturated with cold ethanol, and recrystallized from ethanol, to yield the 1-methyl-β-oxo-2-pyrrolpropionitrile melting at 107°–109°.

EXAMPLE 2

By treatment of equivalent amounts of concentrated aqueous solutions of sodium, potassium or calcium hydroxide with 1-methyl-β-oxo-α-phenylcarbamoyl-2-pyrrolpropionitrile, filtering the mixture and evaporating it to dryness, the three corresponding metal salts are obtained. These appear to have no well-defined crystalline properties or melting points, although they can be reprecipitated from ethanolic solution by addition of diethyl ether. They are water soluble and show the following infrared bands:

| Na - salt: | 4.57; 6.17 and 6.29μ; |
|---|---|
| K - salt: | 4.58; 6.17 and 6.30μ; |
| Ca - salt: | 4.55; 6.13 and 6.23μ; |

In each case an aqueous solution of the salt gives back said identical free compound (m.p. 174°–175°) upon treatment with hydrochloric acid.

EXAMPLE 3

The suspension of 21.4 g of 1-methyl-β-oxo-α-phenylcarbamoyl-2-pyrrolpropionitrile in 100 ml of absolute ethanol is combined with 11.68 ml of trisethanolamine in 25 ml of ethanol and the solution is warmed until dissolution occurs. It is filtered hot, allowed to cool to room temperature while stirring, the resulting suspension chilled to 10°, filtered and the residue washed with 25 ml of cole ethanol, to yield the corresponding trishydroxy-ethyl-ammonium salt melting at 115°–117°.

EXAMPLE 4

To 500 ml of ethereal diazomethane, generated from 10.3 g of N-nitroso-N-methylurea with 35 ml of 45% aqueous potassium hydroxide and dried over such pellets, 3.8 g of 1-methyl-β-oxo-α-phenylcarbamoyl-2-pyrrolpropionitrile are added. After the nitrogen evolution has ceased, the solution is filtered and evaporated. The residue is triturated with diethyl ether and recrystallized from ethyl acetate, to yield the corresponding methylenol ether, i.e. the 1-methyl-β-methoxy-α-phenylcarbamoyl-2-pyrrolacrylonitrile melting at 121°–122°.

EXAMPLE 5

To the suspension of 4.0 g of 1-methyl-β-oxo-2-pyrrolpropionitrile in 70 ml of toluene and 3.2 g of triethylamine, 3.7 g of p-fluorophenylisocyanate are added while stirring. The mixture is warmed on the steam cone until dissolution and the red-brown solution is allowed to stand overnight at room temperature. It is evaporated on the steam cone, the residue taken up in methanol and the solution poured into the mixture of 8 ml of 5 N hydrochloric acid and 300 ml of water. The precipitated crystals are collected, washed with water, dried, triturated with methanol and recrystalllized from ethyl acetate, to yield the 1-methyl-β-oxo-α-(p-fluorophenylcarbamoyl)-2-pyrrolpropionitrile melting at 198°–199°.

EXAMPLE 6

The mixture of 1.1 g of 1-methyl-β-oxo-α-ethoxycarbonyl-2-pyrrolpropionitrile, 1.1 g of aniline and 60 ml of xylene, is refluxed for 4½ hours. After standing and cooling to room temperature overnight, the solution is filtered, evaporated and the residue recrystallized from methanol, to yield the 1-methyl-β-oxo-α-phenylcarbamoyl-2-pyrrolpropionitrile melting at 173°–174°; it is identical with that obtained according to Example 1.

The starting material is prepared as follows: To the solution of 10 g of 1-methylpyrrole-2-carboxylic acid in 650 ml of dry diethyl ether and 8.5 g of anhydrous triethylamine, the solution of 6.0 ml of thionyl chloride in 50 ml of diethyl ether is gradually added while stirring. After 30 minutes the mixture is filtered, the residue washed with diethyl ether, the filtrate concentrated to a smaller volume, again filtered, and finally evaporated under reduced pressure, to yield the corresponding acid chloride.

The solution thereof in 20 ml of ethyleneglycol dimethyl ether is slowly added to the solution prepared from the suspension of 7.2 g of 50% sodium hydride in mineral oil (washed with petroleum ether) in 50 ml of dimethylformamide and 20 g of ethyl cyanoacetate while stirring and cooling. The moderately exothermic reaction is aided by warming the mixture briefly on the steam cone. After standing overnight, it is treated with water, acidified with 5 N hydrochloric acid and extracted with diethyl ether. The extract is washed with water, dried, evaporated and the residue triturated and recrystallized from diethyl ether, to yield the 1-methyl-$\beta$-oxo-$\alpha$-ethoxycarbonyl-2-pyrrolpropionitrile melting at 74°–77°.

The same product is obtained by acylation with the mixed anhydride, i.e. by substituting in the above sequence the thionyl chloride with the equivalent amount of ethyl chloroformate.

EXAMPLE 7

The mixture of 5.7 g of 1-methyl-$\beta$-oxo-$\alpha$-ethoxycarbonyl-2-pyrrolpropionitrile, 3,6 g of p-aminophenol and 300 ml of xylene is refluxed for 2 hours and filtered hot. The filtrate is chilled, the crystals formed collected and recrystallized from methanol, to yield the 1-methyl-$\beta$-oxo-$\alpha$-(p-hydroxyphenylcarbamoyl)-2-pyrrolpropionitrile melting at 182°–184°.

EXAMPLE 8

To the suspension of 0.8 g of 50% sodium hydride in mineral oil (washed with petroleum ether) in 10 ml of 1,2-dimethoxyethane, 2.9 g of 1-benzyl-$\beta$-oxo-2-pyrrolpropionitrile in 30 ml of 1,2-dimethoxyethane are added, followed by 2.7 g of p-chlorophenylisocyanate while stirring. After standing at room temperature overnight, the mixture is evaporated, the residue taken up in water, the solution filtered and acidified with 5 N hydrochloric acid. The yellow precipitate formed is collected, washed with water, triturated with methanol and recrystallized from ethyl acetate, to yield the 1-benzyl-$\beta$-oxo-$\alpha$-(p-chlophenylcarbamoyl)-2-pyrrolpropionitrile melting at 214°–215°.

The starting material is prepared as follows: 7.5 g of pyrrole-2-carboxylic acid methyl ester in 25 ml of dimethylformamide are added to the suspension prepared from 3.4 g of 50% sodium hydride in mineral oil, washed with petroleum ether and suspended in 20 ml of dimethylformamide while stirring. Thereupon 8.5 ml of benzyl chloride are added and stirring is continued at ambient temperature overnight. The mixture is treated with water, extracted with diethyl ether, the extract washed with aqueous sodium hydroxide and water, dried and evaporated to yield the 1-benzylpyrrole-2-carboxylic acid methyl ester as an oil. (A purified sample thereof melts at 31°–32°).

The solution of 9.3 g thereof in 15 ml of acetonitrile and 25 ml of dimethylformamide is added to the suspension prepared from 4 g of 50% sodium hydride in mineral oil, washed with petroleum ether and suspended in 25 ml of dimethylformamide, while stirring. The mixture is warmed on the steam cone for 30 minutes, during which a dark red solution forms. It is allowed to stand overnight at room temperature, combined with water, filtered, washed with diethyl ether and acidified with 5 N hydrochloric acid. The crystals formed are collected, washed with water, dried, triturated with diethyl ether and recrystallized from methanol, to yield the 1-benzyl-$\beta$-oxo-2-pyrrolpropionitrile melting at 119°–120°.

EXAMPLE 9

To the solution of 4.0 g of phenylcarbamoyl-acetonitrile in 50 ml of dimethylformamide 28 g of potassium tert. butoxide are added while stirring under nitrogen. After 2 hours the resulting suspension is cooled to 5° and 4.0 g of 1-methylpyrrol-2-carboxylic acid chloride (U.S. Pat. No. 3,551,571) are added during 10 minutes. The mixture is stirred for 18 hours at room temperature, poured into 300 ml of ice water and the precipitate formed filtered off. It is washed with water, dried and recrystallized from ethanol, to yield the 1-methyl-$\beta$-oxo-$\alpha$-phenylcarbamoyl-2-pyrrolpropionitrile melting at 172°–174°; it is identical with that obtained according to Example 1.

The starting material is prepared as follows: To the mixture of 42.53 g of cyanoacetic acid, 46.56 g of aniline and 500 ml of acetonitrile, the solution of 113.7 g of N,N-dicyclohexyl-carbodiimide in 500 ml of acetonitrile is added during 30 minutes while stirring under nitrogen. After 3 hours the resulting suspension is filtered, the residue washed with 200 ml of acetonitrile and the filtrates are evaporated. The residue is triturated with 500 ml of diethyl ether and 50 ml of ethyl acetate, filtered off and dried, to yield the phenylcarbamoylacetonitrile melting at 200°–202°.

EXAMPLE 10

To the suspension of 1,135 g of 1-methyl-$\beta$-oxo-2-pyrrolpropionitrile in 17,000 ml of dry toluene, 913 g of anhydrous triethylamine are added, followed by 913 g of phenylisocyanate while stirring under nitrogen. The dark brown solution formed is stirred at room temperature overnight and evaporated at 60°–70°/10 mm Hg. The residue is taken up in 1,400 ml of methanol and the solution treated with 1,400 ml of 6 N hydrochloric acid in 4,200 ml of water. The suspension is cooled to 15°–20° for 20 minutes, filtered and the residue washed twice with 1,800 ml of water, twice with 1,000 ml of isopropanol and 13 times with 1,000 ml of diethyl ether. This crude residue is dried at 60° and 5 mm Hg to constant weight and 1,960 g thereof are dissolved in 44,400 ml of methylene chloride at room temperature. The solution is treated with 400 g of activated charcoal, filtered and the filtrate evaporated. The residue is triturated with 12,000 ml of anhydrous ethanol, the suspension filtered at 20°, washed 4 times with 1,000 ml of anhydrous ethanol and dried at 60° and 5 mm Hg, to yield the 1-methyl-$\beta$-oxo-$\alpha$-phenylcarbamoyl-2-pyrrolpropionitrile melting at 172°–174°, it is identical with that of Examples 1, 6 or 9.

1,801 g thereof are suspended in 10,500 ml of anhydrous ethanol and 1,108 g of triethanolamine are added. The mixture is stirred and heated until dissolution occurs, whereupon it is slowly cooled to 20°. The precipitate formed is filtered off, washed twice with 1,000 ml of cold anhydrous ethanol and dried at 45° and 0.1 mm Hg, to yield the corresponding tris-hydroxyethylammonium salt melting at 115°–117°; it is identical with that of Example 3.

The starting material is prepared as follows: The solution of 1,325 g of 1-methylpyrrole-2-carboxylic acid in 2,400 ml of dimethylformamide is added to the suspension prepared from 568.5 g of 50% sodium hydride in mineral oil and 2,400 ml of dimethylformamide, while stirring under nitrogen and cooling with ice. Thereupon 1,000 ml of dimethylformamide are added, followed by 4,316 g of methyl iodide while stirring and keeping the temperature below 88°. Stirring is continued overnight at room temperature, whereupon the mixture is cooled to 10° and combined with 10,600 ml of water. It is extracted thrice with 5,300 ml of diethyl ether, the extract washed with 5,300 ml of 10% aqueous sodium carbonate and 5,300 ml of water, dried and evaporated, to yield the 1-methylpyrrole-2-carboxylic acid methyl ester as an oil.

The solution of 1,604 g thereof in 2,650 ml of acetonitrile is rapidly added to the suspension prepared from 1,017 g of 50% sodium hydride in mineral oil and 2,650 ml of dimethylformamide, while stirring under nitrogen. The mixture is warmed to 81° for 2 hours and cooled to 10°, whereupon 25,400 ml of water are added during 15 minutes. It is washed thrice with 9,000 ml of diethyl ether, stirred for 45 minutes at 10 mm Hg to remove diethyl ether, and acidified with 6,400 ml of 6 N hydrochloric acid. The crystals formed are collected, washed 4 times with 2,400 ml of water, and once with 2,400 ml of isopropanol, and dried at 60° and 5 mm Hg, to yield the 1-methyl-$\beta$-oxo-2pyrrolpropionitrile melting at 106°–108°.

EXAMPLE 11

To the filtered solution of 4.4 g of 2,6-dichlorophenylisocyanate in 30 ml of toluene is added 2.5 g of 1-methyl-$\beta$-oxo-2-pyrrolpropionitrile and 2.1 g of triethylamine while stirring. The mixture is allowed to stand overnight at room temperature, whereupon it is filtered. The solids are washed with toluene and diethyl ether, taken up in 50 ml of methanol and the solution poured into the mixture of 6 ml of 5 N hydrochloric acid and 300 ml of water. The crystals formed are collected, washed with water, dried, triturated with ethanol, and recrystallized from methanol, to yield the 1-methyl-$\beta$-oxo-$\alpha$-(2,6-dichlorophenylcarbamoyl)-2-pyrrolpropionitrile melting at 196°–199°.

EXAMPLE 12

The suspension of 2.0 g of the 1-methyl-$\beta$-oxo-2-pyrrolpropionitrile in 50 ml of toluene and 1.6 g of triethylamine is treated with 2.1 g of p-methoxyphenylisocyanate. The mixture is warmed gently until all is dissolved and allowed to stand overnight at room temperature. It is evaporated, the residue is taken up in methanol and combined with 10 ml of 10% aqueous sodium hydroxide and 250 ml of water. The alkaline solution is filtered, acidified with 5 N hydrochloric acid and the precipitate formed collected. It is washed with water, dried, triturated with warm methanol-ethyl acetate, and recrystallized from ethyl acetate, to yield the 1-methyl-$\beta$-oxo-$\alpha$-(p-methoxyphenylcarbamoyl)-2-pyrrolpropionitrile melting at 192°–193°.

In the analogous manner the 1-methyl-$\beta$-oxo-$\alpha$-(p-methylthiophenylcarbamoyl)-2-pyrrolpropionitrile is prepared, melting at 167°–168°.

EXAMPLE 13

The solution of 4.9 g of the 1-methyl-$\beta$-oxo-2-pyrrolpropionitrile in 50 ml of toluene, 5 ml of dimethylsulfoxide and 4 g of triethylamine is treated with the solution of 5.7 g of p-nitrophenylisocyanate in the minimum amount of toluene while stirring. After standing overnight it is evaporated and the residue taken up in methanol. The solution is filtered, diluted with water and 6 ml of triethylamine, washed with ethyl acetate, and the washings extracted once with 5% aqueous sodium hydroxide. The combined aqueous solutions are acidified with 5 N hydrochloric acid and the precipitate collected. It is washed with water, triturated with methanol-ethanol and recrystallized from dimethylformamide, to yield the 1-methyl-$\beta$-oxo-$\alpha$-(p-nitrophenylcarbamoyl)-2-pyrrolpropionitrile melting at 245°–250° with decomposition.

The solution of 2.0 g thereof in 220 ml of ethanol and 2 ml of triethylamine is hydrogenated over 0.5 g of 10% palladium on carbon at 3.5 atm. and room temperature for 50 minutes. The filtered solution is evaporated, the residue taken up in water, 1 ml of triethylamine is added and the solution washed with ethyl acetate and diethyl ether. It is acidified with 5 N hydrochloric acid, the precipitate collected, washed with water, dried, and recrystallized from aqueous methanol, to give the 1-methyl-$\beta$-oxo-$\alpha$-(p-aminophenylcarbamoyl)-2-pyrrolpropionitrile melting at 193°–195° with decomposition.

0.5 g thereof are dissolved in 10 ml of acetic anhydride, the solution refluxed for 10 minutes and evaporated. The residue is triturated with diethyl ether and recrystallized from methanol-ethyl acetate, to yield the 1-methyl-$\beta$-acetoxy-$\alpha$-(p-acetylaminophenylcarbamoyl)-2-pyrrolacrylonitrile melting at 178°–179°.

EXAMPLE 14

The mixture of 2.1 g of 1-ethyl-$\beta$-oxo-2-pyrrolpropionitrile, 25 ml of toluene and 1.6 g of triethylamine is treated with 1.6 g of phenylisocyanate while stirring. It is allowed to stand overnight at room temperature, evaporated and the residue dissolved in methanol. The solution is poured into 300 ml of water containing 5 ml of 5 N hydrochloric acid and the precipitate is collected. It is dissolved in 5% aqueous sodium hydroxide, the solution filtered, the filtrate re-acidified, the solids collected, washed with water, dried and recrystallized from ethanol, to yield the 1-ethyl-$\beta$-oxo-$\alpha$-phenylcarbamoyl-2-pyrrolpropionitrile melting at 144°–145°.

The starting material is prepared as follows. To the suspension, prepared from 9.1 g of 50% sodium hydride in mineral oil, washed with petroleum ether and suspended in 50 ml of dimethylformamide, is gradually added 20 g of pyrrole-2-carboxylic acid methyl ester in 50 ml of dimethylformamide while stirring and cooling with ice. After dissolution 25 ml of ethyl bromide are added while warming gently to initiate the exothermic reaction. When it subsided, 5 ml additional ethyl bromide are added and the mixture is allowed to stand overnight. After treatment with water it is extracted with diethyl ether, the extract washed with water, dried, filtered and evaporated to give the oily 1-ethylpyrrole-2-carboxylic acid methyl ester.

The solution of 10 g thereof in 25 ml of acetonitrile and 25 ml of dimethylformamide is added to the suspension of 5.5 g of 50% sodium hydride (washed with petroleum ether) in 15 ml of dimethylformamide and the mixture is heated at the steam cone for 15 minutes while stirring. After standing overnight it is treated with water, filtered, acidified with 5 N hydrochloric acid and the residue collected. It is washed with water, and recrystallized from ethanol, to give the 1-ethyl-$\beta$-oxo-2-pyrrolpropionitrile melting at 77°–79°.

EXAMPLE 15

The solution of 2.5 g of 1-isobutyl-$\beta$-oxo-2-pyrrolpropionitrile in 30 ml of toluene and 1.6 g of triethylamine is treated with 1.6 g of phenylisocyanate while stirring. After standing overnight the mixture is filtered and the residue dissolved in 5% aqueous sodium hydroxide. The solution is filtered, acidified with 5 N hydrochloric acid and extracted with diethyl ether-ethyl acetate. The organic solution is washed with water, dried, evaporated, the residue triturated with ethanol and recrystallized from methanol, to give the 1-isobutyl-β-oxo-α-phenylcarbamoyl-2-pyrrolpropionitrile melting at 134°–136°.

The starting material is prepared as follows: 13 g of pyrrole-2-carboxylic acid methyl ester are added to the suspension prepared from 5.5 g of 50% sodium hydride in mineral oil, washed with petroleum ether and suspended in 70 ml of dimethylformamide, while stirring. Thereupon 40 g of isobutyl bromide are added and stirring is continued at the steam cone for 10 minutes. After standing overnight, the mixture is treated with water, extracted with diethyl ether, the extract washed with water, dried and evaporated, to yield the 1-isobutylpyrrole-2-carboxylic acid methyl ester as an oil.

The solution of 10 g thereof in 15 ml of acetonitrile is added to the suspension prepared from 5 g of 50% sodium hydride in mineral oil, washed with petroleum ether and suspended in 25 ml of dimethylformamide, while stirring. After the effervescent reaction subsided, the mixture is warmed on the steam cone for 30 minutes, during which time the sodium hydride is consumed. After standing overnight at room temperature, the mixture is combined with water and acidified with 5 N hydrochloric acid. It is extracted with diethyl ether, the extract washed with water, dried and evaporated, to yield the 1-isobutyl-β-oxo-2-pyrrolpropionitrile as an oil.

EXAMPLE 16

To the solution of 1.6 g of 1,3,5-trimethyl-4-ethoxycarbonyl-β-oxo-2-pyrrolpropionitrile in 30 ml of dry toluene and 0.8 g of anhydrous triethylamine, 0.8 g of phenylisocyanate are added while stirring. The mixture is allowed to stand 10 minues at the steam cone and at room temperature overnight. It is evaporated, the residue taken up in methanol and the solution treated with 2 ml of 5 N hydrochloric acid and 200 ml of water. The crystals formed are collected, washed with water, triturated with methanol-ethanol and recrystallized from methanol, to yield the 1,3,5-trimethyl-4-ethoxycarbonyl-β-oxo-α-phenylcarbamoyl-2-pyrrolpropionitrile melting at 164°–166°.

Analogously its p-(fluoro or chlorophenyl)-analogs are prepared, melting at 178°–179° and 238°–241° (dec.) respectively.

The starting material is prepared as follows: To the suspension of 3.6 g of 50% sodium hydride in mineral oil (washed with petroleum ether) and 50 ml of dimethylformamide, 16 g of 3,5-dimethylpyrrole-2,4-dicarboxylic acid diethyl ester in 25 ml of dimethylformamide are added portionwise while stirring. After the sodium hydride is consumed 40 ml of methyl iodide are added and the mixture is allowed to stand overnight at room temperature. It is treated with water, the solids formed collected and air-dried to remove excess methyl iodide. They are rewashed with water, dried and recrystallized from ethanol, to afford the 1,3,5-trimethylpyrrole-2,4-dicarboxylic acid diethyl ester.

The solution of 13.9 g thereof in 30 ml of acetonitrile and 30 ml of dimethylformamide is added to the suspension of 5.5 g of 50% sodium hydride in mineral oil (washed with petroleum ether) in 60 ml of dimethylformamide while stirring. The mixture is warmed on the steam cone for 15 minutes and the solution formed allowed to stand overnight. After treatment with water, the aqueous solution is filtered and acidified with 5 N hydrochloric acid. The precipitate is collected, washed with water, triturated with ethanol and recrystallized from ethanol, to yield the 1,3,5-trimethyl-4-ethoxycarbonyl-β-oxo-2-pyrrolpropionitrile melting at 105°–107°.

EXAMPLE 17

The solution of 0.3 g of 5-(1-methyl-2-pyrrolyl)-4-phenylcarbamoylisoxazole, 10 ml of 5% aqueous sodium hydroxide and the minimum amount of ethanol, is warmed on the steam cone for 5 minutes. It is filtered, acidified with 5 N hydrochloric acid and the crystals formed collected. They are washed with water and triturated with methanol to give the 1-methyl-β-oxo-α-phenylcarbamoyl-2-pyrrolpropionitrile melting at 170°–172°; it is identical with that prepared as described previously, i.e. Examples 1, 6, 9 or 10.

The starting material is prepared as follows: To the solution of 17 g of 1-methylpyrrole in 400 ml of 1,2-dichloroethane is added 28 g of anhydrous aluminum chloride in portions, while stirring and cooling to 10°–15°, followed by 27 g of ethyl malonyl chloride in 50 ml of dichloroethane at such a rate to keep the temperature between 10° and 15°. After stirring for 3.5 hours the temperature is allowed to rise slowly to 32° and the mixture is allowed to stand overnight at room temperature. It is treated with water, shaken, the organic layer separated, washed twice with water, dried and evaporated. The residual dark brown oil is distilled and the fraction boiling at 105–112/0.25 mm Hg collected, to yield the 1-methyl-β-oxo-2-pyrrolpropionic acid ethyl ester.

The mixture of 3.6 g thereof and 3.9 g of N,N'-diphenylformamidine is heated to 145°–165° over the course of 2.5 hours. The cooled, brittle glass obtained is pulverized, triturated with diethyl ether and recrystallized from ethanol-ethyl acetate, to yield the 1-methyl-β-oxo-α-anilinomethylene-2-pyrrolpropionic acid anilide melting at 178°–180°.

The mixture of 1.4 g thereof, 1.1 g of hydroxylamine hydrochloride, 1.2 g of pyridine and 150 ml of ethanol is refluxed for 7 hours. After standing overnight it is filtered, evaporated and the residue treated with water. The orange oil which separates crystallizes on standing; it is collected, washed with water and recrystallized from ethanol to give the 5-(1-methyl-2-pyrrolyl)-4-phenylcarbamoylisoxazole melting at 100°–103°.

EXAMPLE 18

To the suspension of 1.0 g of 1,3,5-trimethyl-β-oxo-2-pyrrolpropionitrile in 30 ml of dry toluene and 0.7 g of anhydrous triethylamine, 0.75 g of phenylisocyanate are added while stirring. The mixture is warmed for 5 minutes at the steam cone and allowed to stand at room temperature overnight. It is filtered, the residue taken up in methanol and the solution acidified with N hydrochloric acid. The precipitate formed is collected, dissolved in N aqueous sodium hydroxide, re-precipitated with 5 N hydrochloric acid and washed with water, to yield the 1,3,5-trimethyl-β-oxo-α-phenylcarbamoyl-2-pyrrolpropionitrile melting at 172°–174°.

The starting material is prepared as follows: The mixture of 11.9 g of 1,3,5-trimethylpyrrole-2,4-dicarboxylic acid diethyl ester and 50 ml of concentrated sulfuric acid is heated on the steam cone for 1 hour. The resulting solution is poured on to ice, the precipitate collected and washed with water. It it taken up in aqueous sodium carbonate, the solution filtered and the filtrate acidified with 5 N hydrochloric acid. The precipitate formed is collected, washed with water, dried and recrystallized from ethanol, to yield the 1,3,5-trimethyl- 2-carbethoxypyrrole-4-carboxylic acid melting at 197°–198° with decomposition.

7.5 g thereof are heated to 235°–240° while on reflux for 15 minutes and cooled. The residue is taken up in petroleum ether, the solution filtered and evaporated, to yield the 1,3,5-trimethylpyrrole-2-carboxylic acid ethyl ester melting at 38°–40° (reported, in U.S. Pat. No. 2,479,972: b.p. 102°–8°/3–4 mm Hg).

The solution of 4.0 g thereof in 10 ml of acetonitrile is added to the suspension prepared from 2.0 g of 50% sodium hydride in mineral oil, washed with petroleum ether and suspended in 15 ml of dimethylformamide, while stirring. The mixture is warmed on the steam cone for 25 minutes and allowed to stand for 3 hours at room temperature. It is combined with water, the aqueous solution washed with diethyl ether and acidified with 5 N hydrochloric acid. The crystals are collected, washed with water, dried and recrystallized from ethanol with the aid of charcoal, to yield the 1,3,5-trimethyl-$\beta$-oxo-2-pyrrolpropionitrile melting at 106°–107°.

Analogously the 1,3,5-trimethyl-$\beta$-oxo-$\alpha$-(p-fluorophenylcarbamoyl)-2-pyrrolpropionitrile is obtained, melting after recrystallization from methanol-ethanol (1:1) at 184°–186°.

EXAMPLE 19

The suspension of 1.0 g of 1,2,5-trimethyl-$\beta$-oxo-3-pyrrolpropionitrile, 40 ml of toluene and 0.7 g of triethylamine is treated with 0.75 g of phenylisocyanate and warmed for 5 minutes on the steam cone until all is dissolved. After standing overnight, the precipitate formed is collected, taken up in methanol, and the solution added to the mixture of 3 ml of 5 N hydrochloric acid and 250 ml of water. The crude product formed is collected, washed with water, dissolved in 5% aqueous sodium hydroxide, filtered, and the alkaline filtrate acidified with 5 N hydrochloric acid. The precipitate is collected, washed with water, air-dried and recrystallized from ethanol, to yield the 1,2,5-trimethyl-$\beta$-oxo-$\alpha$-phenylcarbamoyl-3-pyrrolpropionitrile melting at 158°–160°.

Similarly, the crude 1,2,5-trimethyl-$\beta$-oxo-$\alpha$-(p-fluorophenylcarbamoyl)-3-pyrrolpropionitrile is obtained. It is dissolved in aqueous sodium bicarbonate, reprecipitated with 5 N hydrochloric acid and recrystallized from ethanol; mp. 171°–172°.

The starting material is prepared as follows: The solution of 7.6 g of 1,2,5-trimethylpyrrole-3-carboxylic acid ethyl ester [Ber. 56,2374 (1923)], recrystallized from methanol (mp. 65°–66°), in 20 ml of acetonitrile, is added to the suspension of 4.0 g of 50% sodium hydride in mineral oil, and 11 ml of dimethylformamide. The mixture is heated on the steam cone while stirring for 20 minutes, and the resulting suspension allowed to cool to room temperature during 90 minutes. It is poured into 200 ml of ice water, the aqueous alkaline solution filtered, and the filtrate acidified with 18% hydrochloric acid, while chilling with ice. The precipitate is collected, washed with water, air-dried, triturated with diethyl ether and recrystallized from methanol, to yield the 1,2,5-trimethyl-$\beta$-oxo-3-pyrrolpropionitrile melting at 140°–141°.

EXAMPLE 20

According to the methods illustrated by the previous examples, preferably Example 1, 4, 8 and 10, the following compounds of Formula II with $R_2=R_3=H$ are obtained from equivalent amounts of the corresponding starting materials:

| No. | $R_1$ | $R_4$ | $R_5$ | Recryst. from | m.p. °C. |
|---|---|---|---|---|---|
| 1 | $CH_3$ | 2-$CH_3$ | 6-$CH_3$ | ethanol | 170–171 |
| 2 | $CH_3$ | 3-F | H | ethyl acetate | 191–192 |
| 3 | $CH_3$ | 3-Cl | H | ethyl acetate | 192–193 |
| 4 | $CH_3$ | 4-Cl | H | ethyl acetate | 205–207 |
| 5 | $CH_3$ | 3-$CF_3$ | H | methanol | 185–186 |
| 6 | $CH_3$ | 2-F | 4-F | methanol | 136–138 |
| 7 | $CH_3$ | 4-F | 3-Cl | ethyl acetate | 215–216 |
| 8 | $CH_3$ | 2-Cl | 4-Cl | ethyl acetate | 160–162 |
| 9 | $CH_3$ | 3-Cl | 4-Cl | dimethylformamide | 217–219 |
| 10 | benzyl | H | H | ethyl acetate | 188–189 |
| 11 | benzyl | 4-F | H | ethyl acetate | 203–204 |
| 12 | $C_2H_5$ | 4-F | H | methanol | 156–157 |
| 13 | $C_2H_5$ | 4-Cl | H | ethanol | 160–161 |
| 14 | i-butyl | 4-F | H | methanol | 162–163 |

EXAMPLE 21

Preparation of 10,000 tablets each containing 100 mg of the active ingredient:

| Formula: | |
|---|---|
| Tris-hydroxyethylammonium 1-methyl-$\beta$-oxo-$\alpha$-phenylcarbamoyl-2-pyrrolpropionitrile | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches with 10.3 mm diameter, uppers bisected.

Analogously tablets are prepared, containing one of the other compounds illustrated by the previous examples.

EXAMPLE 22

Preparation of 1,000 capsules each containing 25 mg of the active ingredient:

| Formula: | |
|---|---|
| 1-Methyl-$\beta$-oxo-$\alpha$-(p-fluorophenylcarbamoyl)-2-pyrrolpropionitrile | 25.0 g |
| Lactose | 207.0 g |
| Modified starch | 80.0 g |
| Magnesium stearate | 3.0 g |

PROCEDURE

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 315 mg of said mixture each, using a capsule filling machine.

Analogously capsules are prepared, containing 25-100 mg of the other compounds disclosed and illustrated herein, especially those of Formula II, or the alkali metal, zinc, tri-lower alkylammonium or tris-hydroxyethylammonium salts thereof.

What is claimed is:

1. A 1-substituted-$\beta$-oxo-$\alpha$-phenylcarbamoyl-pyrrol-propiontrile of the formula

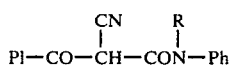

wherein Pl is 2- or 3-pyrrolyl substituted in 1-position by lower alkyl or Ph-lower alkyl and being unsubstituted in the remaining 3 positions, or substituted therein by lower alkyl and/or one carboxy or lower carbalkoxy; Ph is phenyl, unsubstituted or substituted by one to three identical or different members selected from lower alkyl, lower alkoxy, lower alkylthio, hydroxy, halogeno, trifluoromethyl, nitro, amino or lower alkanoylamino; and R is hydrogen or lower alkyl; a lower alkylenol ether or lower alkanoylenol ester, or a salt thereof derived from a pharmaceutically acceptable base.

2. A compound as claimed in claim 1, in which formula Pl is 1-lower (alkyl or Ph-alkyl)-2 or 3-pyrrolyl, unsubstituted in the remaining positions, or substituted therein by one or two lower alkyl groups or one carboxy or lower carbalkoxy group; Ph is phenyl, or phenyl substituted by one or two of the same or different members selected frm lower alkyl, lower alkoxy, lower alkylthio, hydroxy, halogeno, trifluoromethyl, nitro, amino and lower alkanoylamino; and R is hydrogen or lower alkyl; or a lower alkylenol ether or alkanoylenol ester, or a salt thereof derived from a pharmaceutically acceptable base.

3. A compound as claimed in claim 1 and corresponding to the formula

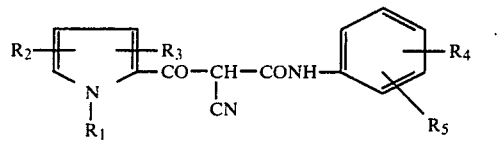

wherein $R_1$ is lower alkyl, each of $R_2$ and $R_3$ is hydrogen or lower alkyl and each of $R_4$ and $R_5$ is hydrogen, lower alkyl, lower alkoxy, hydroxy, halogeno or trifluoromethyl; or a salt thereof derived from a pharmaceutically acceptable base.

4. A compound as claimed in claim 3, in which formula $R_1$ is alkyl with up to 4 carbon atoms; each of $R_2$ and $R_3$ is hydrogen; and each of $R_4$ and $R_5$ is hydrogen, alkyl or alkoxy with up to 4 carbon atoms each, fluoro, chloro or trifluoromethyl, or a salt thereof derived from a pharmaceutically acceptable base.

5. A compound as claimed in claim 3, in which formula $R_1$ is methyl, each of $R_2$ and $R_3$ is hydrogen; and each of $R_4$ and $R_5$ is hydrogen, methyl, methoxy, fluoro, chloro or trifluoromethyl; or the sodium, potassium, calcium, triethylammonium or trishydroxyethylammonium salt thereof.

6. A compound as claimed in claim 5, wherein one of $R_4$ and $R_5$ is different from hydrogen and in paraposition of the phenyl ring.

7. A compound as claimed in claim 5 and being the 1-methyl-$\beta$-oxo-$\alpha$-phenylcarbamoyl-2-pyrrolpropionitrile, or the sodium, potassium, calcium, triethylammonium or tris-hydroxyethylammonium salt thereof.

8. An antiinflammatory and antiarthritic pharmaceutical composition comprising a correspondingly effective amount of a compound claimed in claim 1, together with a pharmaceutical excipient.

9. A method of treating inflammatory and arthritic conditions in mammals, which consist in administering to said mammals enterally, parenterally or topically a composition as claimed in claim 8.

* * * * *

UNITED STATES PATENT AND TRADEMARK OFFICE
CERTIFICATE OF CORRECTION

PATENT NO. : 4,256,759
DATED : MARCH 17, 1981
INVENTOR(S) : GORDON N. WALKER

It is certified that error appears in the above-identified patent and that said Letters Patent are hereby corrected as shown below:

CLAIM 1, COLUMN 17, LINE 12 reads:

"propiontrile of the formula"

should read:

-- propionitrile of the formula --

Signed and Sealed this

Nineteenth Day of January 1982

|SEAL|

Attest:

Attesting Officer

GERALD J. MOSSINGHOFF

Commissioner of Patents and Trademarks